(12) United States Patent
Kim et al.

(10) Patent No.: US 11,389,645 B2
(45) Date of Patent: Jul. 19, 2022

(54) CHRONIC IMPLANTABLE NEURAL PROBE ARRAY FOR NEURAL SIGNAL ACQUISITION AND STIMULATION

(71) Applicant: KOREA INSTITUTE OF SCIENCE AND TECHNOLOGY, Seoul (KR)

(72) Inventors: Jinseok Kim, Seoul (KR); Hyungdal Park, Seoul (KR); Woo Hyun Jung, Seoul (KR); Wonsuk Choi, Seoul (KR); Sunyoung Jung, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 588 days.

(21) Appl. No.: 16/548,437

(22) Filed: Aug. 22, 2019

(65) Prior Publication Data
US 2020/0061372 A1    Feb. 27, 2020

(30) Foreign Application Priority Data
Aug. 23, 2018 (KR) .................. 10-2018-0098601

(51) Int. Cl.
*A61N 1/05* (2006.01)
*A61M 31/00* (2006.01)
(Continued)

(52) U.S. Cl.
CPC .............. *A61N 1/0551* (2013.01); *A61B 5/24* (2021.01); *A61B 5/6877* (2013.01);
(Continued)

(58) Field of Classification Search
CPC . A61B 2562/0209; A61B 5/24; A61B 5/6877; A61B 5/6867; A61M 31/002; A61M 2205/054; A61M 31/00; A61N 1/3605; A61N 1/36057; A61N 1/36053; A61N 1/0551; A61N 1/0556
See application file for complete search history.

(56) References Cited

U.S. PATENT DOCUMENTS

| 2010/0016742 A1 | 1/2010 | James et al. |
| 2015/0126843 A1 | 5/2015 | Pemba et al. |

(Continued)

FOREIGN PATENT DOCUMENTS

| JP | 2007518541 A | 7/2007 |
| JP | 5041584 B2 | 10/2012 |

(Continued)

OTHER PUBLICATIONS

Bosun Hwang et al., "Deep ECGNet: An Optimal Deep Learning Framework for Monitoring Metal Stress Using Ultra Short-Term ECG Signals", Telemedicine and e-Health, Oct. 2018, pp. 753-772, vol. 24, No. 10.

(Continued)

*Primary Examiner* — Jon Eric C Morales
(74) *Attorney, Agent, or Firm* — Rabin & Berdo, P.C (57) ABSTRACT

Provided is a neural probe array including a probe which is insertable into a nerve, the probe having a microchannel which induces the regeneration of the nerve, wherein an electrode is installed within the microchannel and is physically isolated from gliosis, and the microchannel is configured to receive a nerve growth factor for regenerating the nerve, and when the probe is inserted into the nerve, the electrode physically isolated from gliosis accomplishes neural signal acquisition and stimulation.

8 Claims, 6 Drawing Sheets

(51) Int. Cl.
 A61N 1/36 (2006.01)
 A61B 5/00 (2006.01)
 A61B 5/24 (2021.01)
(52) U.S. Cl.
 CPC ......... *A61M 31/002* (2013.01); *A61N 1/3605* (2013.01); *A61B 2562/0209* (2013.01); *A61B 2562/227* (2013.01); *A61M 2205/054* (2013.01)

(56) References Cited

U.S. PATENT DOCUMENTS

| | | | |
|---|---|---|---|
| 2016/0338640 | A1 | 11/2016 | Chan et al. |
| 2017/0071551 | A1 | 3/2017 | Jain et al. |
| 2017/0181700 | A1 | 6/2017 | Olivier et al. |
| 2017/0251987 | A1 | 9/2017 | Collier |
| 2017/0360351 | A1 | 12/2017 | Unni et al. |
| 2018/0078189 | A1 | 3/2018 | Chan et al. |
| 2018/0125427 | A1 | 5/2018 | Oh et al. |

FOREIGN PATENT DOCUMENTS

| | | | |
|---|---|---|---|
| KR | 10-1006534 | B1 | 1/2011 |
| KR | 10-1044661 | B1 | 6/2011 |
| KR | 1020110090703 | A | 8/2011 |
| KR | 10-2012-0111242 | A | 10/2012 |
| KR | 10-1223889 | B1 | 1/2013 |
| KR | 10-1264156 | B1 | 5/2013 |
| KR | 10-1306528 | B1 | 9/2013 |
| KR | 10-2014-0075905 | A | 6/2014 |
| KR | 10-1694251 | B1 | 1/2017 |
| KR | 10-2018-0052194 | A | 5/2018 |
| WO | 2005070495 | A2 | 8/2005 |

OTHER PUBLICATIONS

Aaqib Saeed et al., "Personalized Driver Stress Detection with Multi-task Neural Networks using Physiological Signals", Machine Learning for Health Workshop at 31$^{st}$ Conference on Neural Information Processing System, 2017.

Aaqib Saeed et al., "Deep Physiological Arousal Detection in a Driving Simulator using Wearable Sensors", 2017 IEEE International Conference on Data Mining Workshops, pp. 486-493.

Bosun Hwang et al., "Deep ECGNet: An Optimal Deep Learning Framework for Monitoring Mental Stress Using Ultra Short-Term ECG Signals", Telemedicine and e-Health, Oct. 2018, pp. 753-772, vol. 24, No. 10.

CHRONIC IMPLANTABLE NEURAL PROBE ARRAY FOR NEURAL SIGNAL ACQUISITION AND STIMULATION

CROSS-REFERENCE TO RELATED APPLICATION

This application claims priority to Korean Patent Application No. 10-2018-0098601, filed on Aug. 23, 2018, and all the benefits accruing therefrom under 35 U.S.C. § 119, the contents of which in its entirety are herein incorporated by reference.

STATEMENT REGARDING SPONSORED RESEARCH

This research is made in support of STEAM research support (Development of Bidirectional Neural Electrode with Multi-channel and High Selectivity for Chronical Implantation, No. 1711059432) in the National Research Foundation of Korea, the Ministry of Science and ICT of the Republic of Korea, under the supervision of Korean Institute of Science and Technology.

BACKGROUND

1. Field

The present disclosure relates to a neural probe array, and more particularly, to a neural probe array that induces the nerve regeneration through nerve growth factor and physically isolates the regenerated nerve from the surrounding gliosis.

2. Description of the Related Art

Recently, as a neural interface for use in neuroprosthetics or human-machine interfaces (HMIs), studies are made on an ultramicro neural electrode structure that is directly attached to or inserted into the nerve to stimulate or acquire neural signal information from the nerve.

As an example of the ultramicro neural electrode structure, a cuff electrode including a body of a flexible material having a wide area and electrodes embedded in the body is used.

The cuff electrode can detect neural signals or apply neural stimulation through the electrodes formed on the body surface, with the flexible body being wound and secured around the entire nerve surface like a bandage, but it is mainly used for neural stimulation.

However, the cuff electrode is secured such that the body completely wraps the outer surface of the nerve bundle, and compresses parts of the nerve bundle, which inhibits the blood circulation of blood vessels in the epineurium, causing chronic pain. Additionally, the body generally made of a polymer material does not allow oxygen and water to pass through, causing pain or nerve necrosis at the position where the cuff electrode is worn. Accordingly, chronic implantation on the nerve is difficult.

Moreover, as the electrodes acquire neural signals from surface of the nerve bundle, it is impossible to read signals inside of the nerve well and acquire signals at the level of nerve fibers. Accordingly, in general, the cuff electrode includes a limited number of embedded electrodes, which is a factor limiting neuroprosthetic or HMI applications.

To overcome the problem of extraneural electrodes such as cuff electrodes, intrafasicular electrodes designed to be directly inserted into a nerve are used.

Typical examples are a so-called Transverse Intrafascicular Multichannel Electrode/Longitudinal Intra-Fascicular Electrode (TIME/LIFE) in which wire type electrodes are inserted into/pass through a nerve bundle to acquire neural signals, a Utah Electrode Array in which a plurality of probes arranged in the vertical direction is formed in a plate type body and the probes are implanted in a corresponding nerve part, and a sieve electrode in which a plate type body that is thin enough for it to be inserted between cut parts of a nerve has a hole through which the nerve bundle passes by nerve regeneration, and electrodes are arranged in the hole.

Korean Patent Publication No. 10-2018-0052194 (May 18, 2018, "Patent Literature 1") discloses a neural probe structure and a neural probe assembly having the same, and the neural probe structure of Patent Literature 1 is fixed to a nerve to acquire an electrical signal from the nerve or apply an electrical stimulus, and includes a meander shaped body to surround at least a part of the outer periphery of the nerve, and a probe extending from the body and passing through the nerve and having an electrode. Additionally, Patent Literature 1 discloses an example in which the neural probe assembly includes the neural probe structure, the probe passes through the nerve and the body surrounds at least a part of the outer periphery of the nerve, so the neural probe structure is fixed to the nerve.

In the case of the existing neural electrode (surface electrode), gliosis is formed around the neural electrode, and the electrode is completely surrounded by gliosis within six weeks, making it impossible to accomplish neural signal acquisition and stimulation.

SUMMARY

The present disclosure is designed to solve the above-described problem, and therefore the present disclosure is directed to providing a neural probe array that induces the nerve regeneration through nerve growth factor and physically isolates the regenerated nerve from the surrounding gliosis, thereby achieving long-term neural signal acquisition and stimulation.

To solve the above-described problem, a neural probe array of the present disclosure includes a probe which is insertable into a nerve, the probe having a microchannel which induces the regeneration of the nerve, wherein an electrode is installed within the microchannel and is physically isolated from gliosis, and the microchannel is configured to receive a nerve growth factor for regenerating the nerve, and when the probe is inserted into the nerve, the electrode physically isolated from gliosis accomplishes neural signal acquisition and stimulation.

According to an embodiment related to the present disclosure, the neural probe array of the present disclosure may further include a connecting body to which the probe is coupled, the connecting body having an elastic element formed in a meander shape.

The connecting body may be configured to receive a wire electrically connected to the electrode, and the neural probe array of the present disclosure may further include a connector connected to the connecting body, the connector having a terminal electrically connected to the wire.

The microchannel may be formed perpendicular to a lengthwise direction of the probe.

The nerve may be a peripheral nerve.

According to another embodiment related to the present disclosure, the probe may include a support forming one surface of the probe, a first member provided on one surface of the support, and having an electrode receiving element in which the electrode is received, a second member connected to the first member, and having the microchannel, and a third member connected to the second member, and disposed opposite the first member with the microchannel interposed between.

The probe may be a double layer structure having same shapes in combination.

Each of the support and the first member may have a cutout to communicate with the microchannel.

DETAILED DESCRIPTION

Hereinafter, the disclosed embodiments will be described in detail with reference to the accompanying drawings, and identical or similar elements are given identical or similar reference signs and redundant descriptions are omitted herein. As used herein, the suffix "element" is only given or used to ease the drafting of the specification, and does not have any meaning or role for identifying itself. Additionally, in describing the embodiments disclosed herein, when a certain detailed description of relevant known technology is determined to render the key subject matter of the disclosed embodiments ambiguous, its detailed description is omitted herein. Additionally, the accompanying drawings are provided for an easy understanding of the disclosed embodiments, and the technical spirit disclosed herein is not limited by the accompanying drawings, and it should be understood that the present disclosure covers all modifications, equivalents or alternatives falling in the spirit and scope of the present disclosure.

The terms "first", "second", and the like may be used to describe various elements, but the elements are not limited by the terms. Rather, the terms are used to distinguish one element from another.

It will be further understood that when an element is referred to as being "connected to" another element, it can be directly connected to the other element or intervening elements may be present.

As used herein, the singular forms are intended to include the plural forms as well, unless the context clearly indicates otherwise.

It will be understood that the term "comprises" or "includes" when used in this specification, specifies the presence of stated features, integers, steps, operations, elements, components or groups thereof, but does not preclude the presence or addition of one or more other features, integers, steps, operations, elements, components, or groups thereof.

Figure 1:
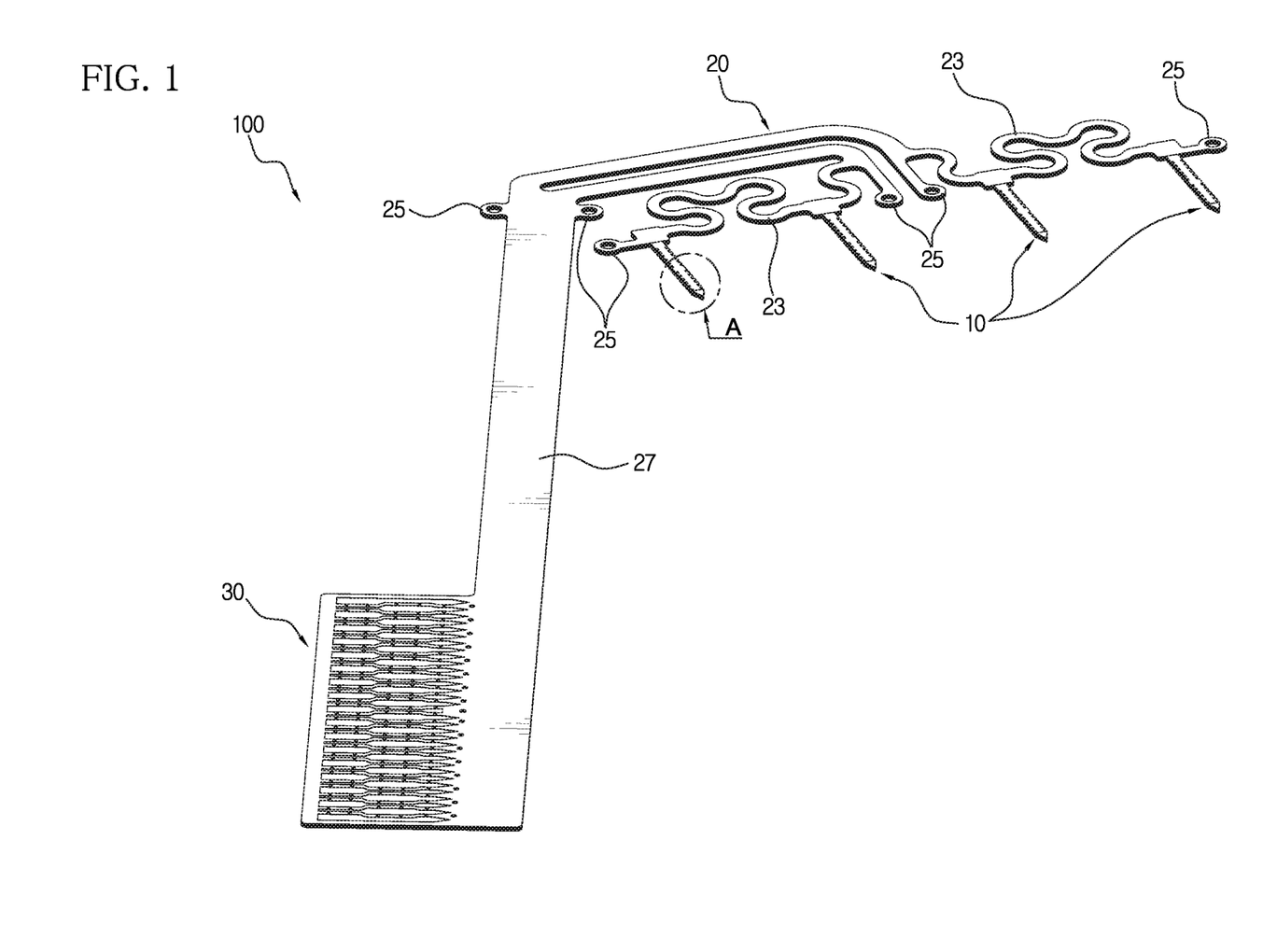
FIG. 1 is a perspective view showing an example of a neural probe array of the present disclosure.
Figure 2A:
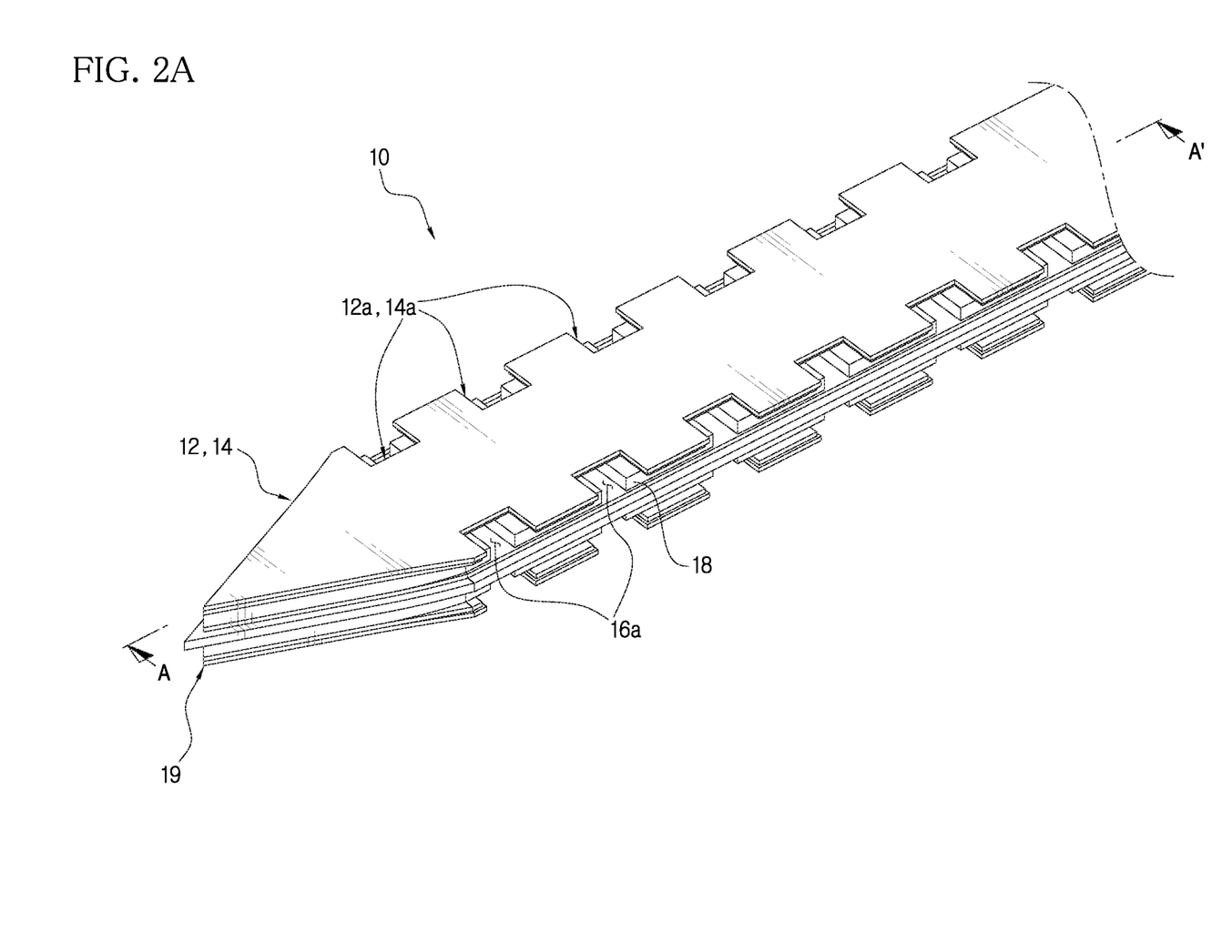
FIG. 2A is an enlarged perspective view of a probe of section A of FIG. 1.
Figure 2B:
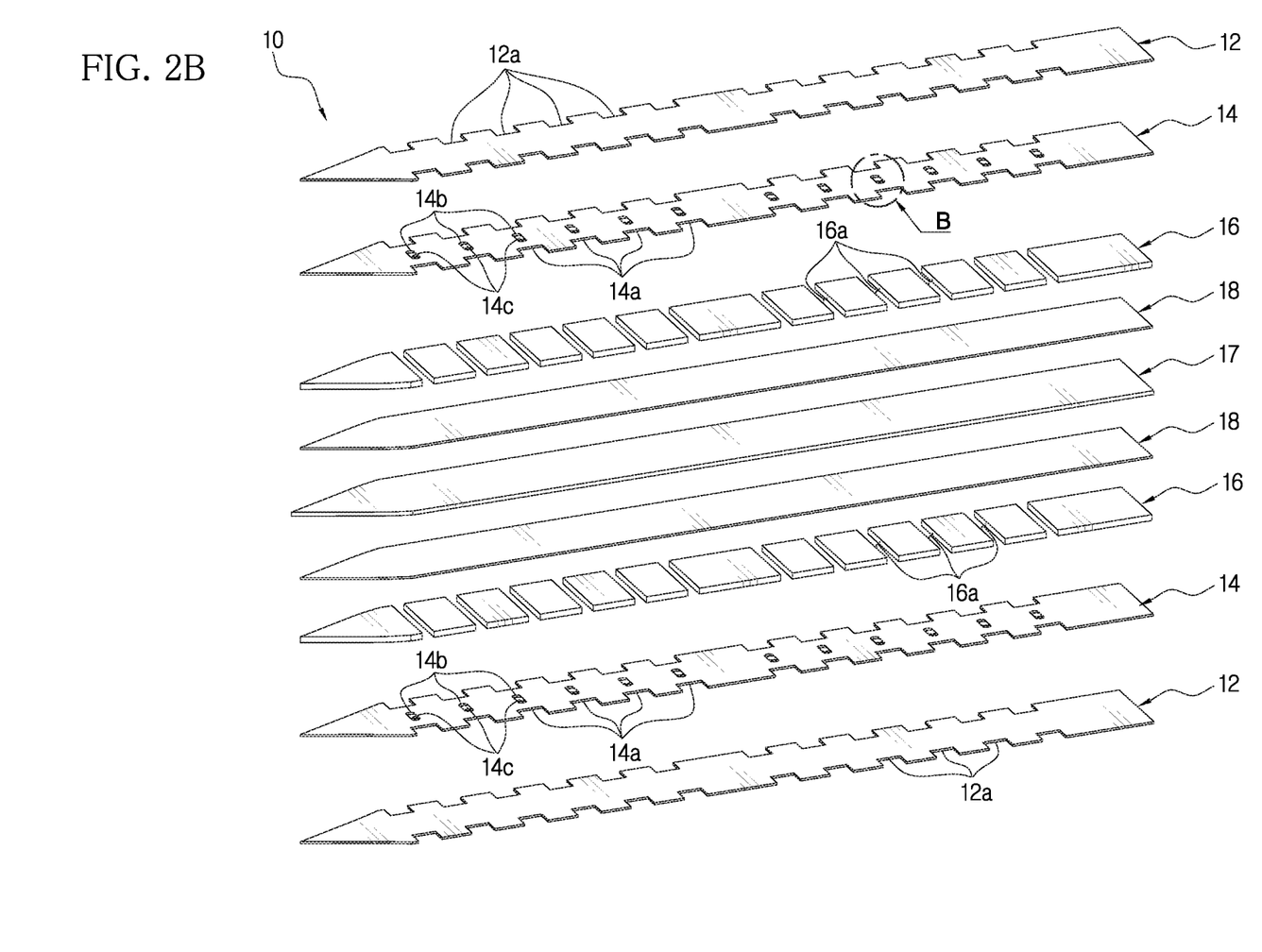
FIG. 2B is an exploded perspective view of the probe of FIG. 2A.
Figure 2C:
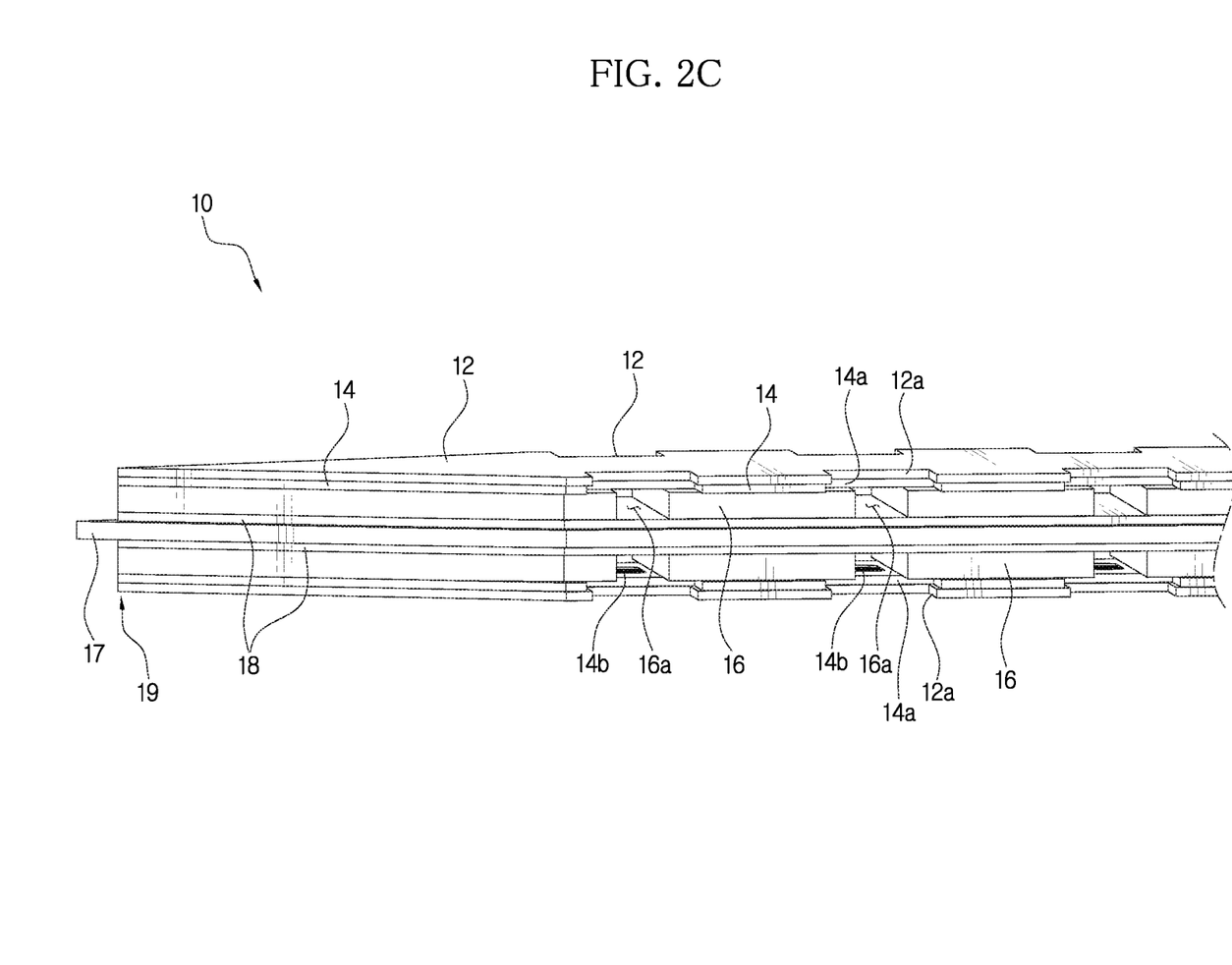
FIG. 2C is a perspective view of the probe of FIG. 2A when viewed from the side.
Figure 2D:
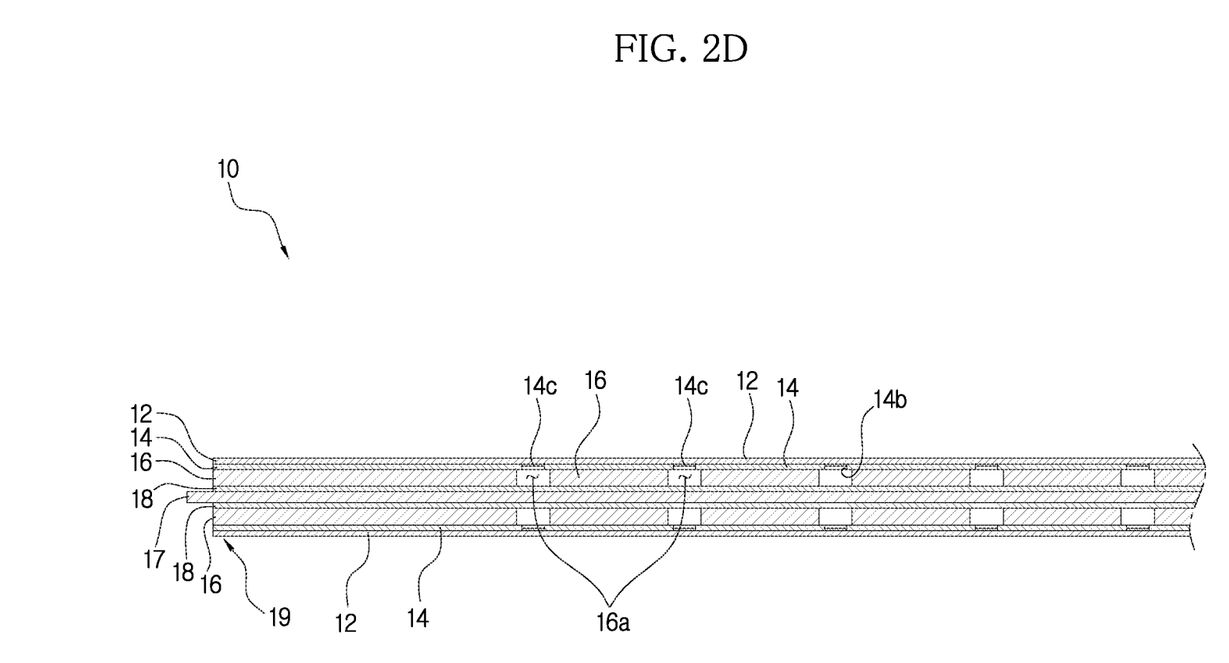
FIG. 2D is a cross-sectional view taken along the line A-A' of FIG. 2A.
Figure 2E:
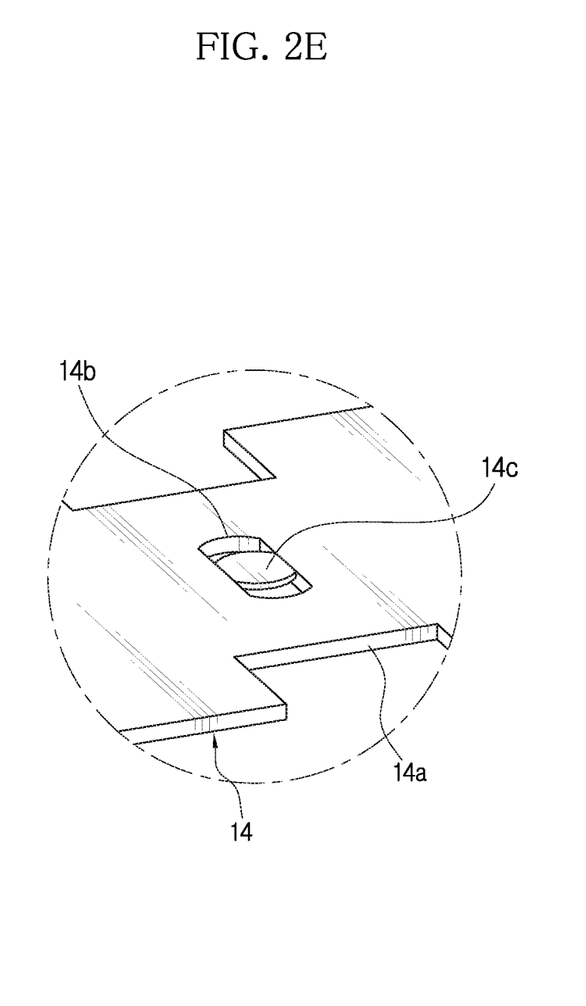
FIG. 2E is an enlarged view of section B of FIG. 2B.

FIG. 1 is a perspective view showing an example of a neural probe array 100 of the present disclosure, FIG. 2A is an enlarged perspective view of a probe 10 of section A of FIG. 1, and FIG. 2B is an exploded perspective view of the probe 10 of FIG. 2A. Additionally, FIG. 2C is a perspective view of the probe 10 of FIG. 2A when viewed from the side, FIG. 2D is a cross-sectional view taken along the line A-A' of FIG. 2A, and FIG. 2E is an enlarged view of section B of FIG. 2B.

Hereinafter, the neural probe array 100 of the present disclosure will be described with reference to FIGS. 1 to 2E.

The neural probe array 100 of the present disclosure includes a probe 10 that can be inserted into a nerve and having microchannel 16a that induces the nerve regeneration.

Electrode 14c is installed within the microchannel 16a provided in the probe 10, the electrode 14c is physically isolated from gliosis, and the microchannel 16a are configured to receive the nerve growth factor. Alternatively, it may be understood that the nerve growth factor is loaded in the microchannel 16a. Although not clearly shown in the drawing, the nerve growth factor induces the nerve regeneration.

The probe 10 has a sharp tip 19 at the end to allow the probe 10 to be easily inserted into the nerve. The probe 10 has a body of a long needle shape, and may have a structure that is easy to be inserted from the outer periphery of the nerve into the nerve in the lengthwise direction.

To minimize damage to the nerve when inserting the probe 10 into the nerve or when the probe 10 is inserted into the nerve, the probe 10 according to this embodiment may be made of a flexible material using polymer, or the surface of the probe 10 may be coated with a flexible material such as polyimide, parylene, silicone and epoxy.

When the probe 10 is made of a flexible material, the probe 10 may have sufficient stiffness to be inserted into the nerve.

Referring to FIGS. 2A and 2C, shown is an example of the microchannel 16a formed perpendicular to the lengthwise direction of the probe 10, allowing nerve regeneration along the formation direction of the microchannel 16a by the nerve growth factor received in the microchannel 16a.

Meanwhile, in the present disclosure, the nerve may be a peripheral nerve.

As shown in FIGS. 2A to 2C, the probe 10 may include a support 12, a first member 14, a second member 16 and a third member 18.

The support 12 is configured to form one surface of the probe 10, and referring to FIGS. 2A and 2B, shown is an example of the support 12 forming an upper surface of the probe 10. Additionally, when the probe is formed with a double layer structure, the support 12 may form an upper surface and a lower surface of the probe 10.

The first member 14 is provided on one surface of the support 12, and has an electrode receiving element 14b in which the electrode 14c is received. For example, as shown in FIG. 2E, the electrode receiving element 14b may be formed of a long hole in which the electrode 14c is installed.

FIGS. 2A to 2C show an example in which the support 12 and the first member 14 have cutouts 12a, 14b respectively, and the cutouts 12a, 14b are formed in communication with the microchannel 16a and serve as guidance for inducing the nerve regeneration.

The second member 16 is connected to the first member 14, and the second member 16 has the microchannel 16a.

The third member 18 is connected to the second member 16 and is disposed opposite the first member 14 with the microchannel 16a interposed between.

The probe 10 may be a double layer structure having the same shapes in combination, and as shown in FIGS. 2B to 2D as an example, a binding element 17 is installed between the two layers of the probe 10 to bind the two layers of the probe 10 together, and the support 12, the first member 14, the second member 16 and the third member 18 have a symmetric structure with respect to the binding element 17.

The probe 10 may be formed as one structure into which the support 12, the first member 14, the second member 16 and the third member 18 are integrated.

Due to the structure of the probe 10 as described above, the neural probe array 100 of the present disclosure accomplishes neural signal acquisition and simulation, with the electrode 14c being physically isolated from gliosis.

Additionally, as the neural probe array 100 of the present disclosure has the electrode probe physically isolated from gliosis, the regenerated peripheral nerve in the microchannel can maintain the performance long-term, thereby allowing chronic implantation.

Meanwhile, the neural probe array 100 of the present disclosure is fixed to the nerve in reliance with the support of the probe 10 for the nerve without any support structure.

Referring to FIG. 1, the neural probe array 100 of the present disclosure may further include a connecting body 20.

The connecting body 20 is formed with the flexible property of the polymer material, and may have sufficient stiffness to allow the probe 10 to be inserted into the nerve.

The probe 10 is coupled to the connecting body 20. Additionally, the connecting body 20 may include an elastic element 23 formed in a meander shape. The connecting body 20 may further include an epineurium fixing element 25 to fix the epineurium.

Referring to FIG. 1, the connecting body 20 connected between the probe 10 and a connector 30 is shown, and an example of the elastic element 23 formed in a meander shape and the epineurium fixing element 25 having a hole is shown. However, the present disclosure is not necessarily limited to this shape.

Additionally, although not shown, a wire (not shown) electrically connected to the electrode 14c may be received in the connecting body 20. A wireless communication device (not shown) may be connected to the wire.

The connecting body 20 may further include a connecting element 27 to which a connector 30 as described below is connected.

The neural probe array 100 of the present disclosure may further include the connector 30.

The connector 30 is connected to the connecting body 20 and includes a terminal electrically connected to the wire. For example, although FIG. 1 shows an example of connection to the connecting element 27 of the connecting body 20, the present disclosure is not necessarily limited to this structure. A power supplier (not shown) may be installed in the terminal of the connector 30, and through this, power may be supplied to the probe 10.

The neural probe array 100 of the present disclosure accomplishes neural signal acquisition and simulation, with the electrode being physically isolated from gliosis.

Additionally, as the neural probe array 100 of the present disclosure has the electrode physically isolated from gliosis, the regenerated peripheral nerve in the microchannel can maintain the performance long-term, thereby allowing chronic implantation.

The neural probe array 100 described above is not limited to the configuration and method of the embodiments described above, and some or all the embodiments may be selectively combined to make various modification.

It is obvious to those skilled in the art that the present disclosure may be embodied in other particular forms without departing from the spirit and essential features of the present disclosure. Therefore, the detailed description should not be interpreted as being limiting in all aspects and should be considered as being exemplary. The scope of the present disclosure should be determined by the reasonable interpretation of the appended claims, and the scope of the present disclosure covers all modifications within the equivalent scope of the present disclosure.

What is claimed is:

1. A neural probe array, comprising:
   a probe which is insertable into a nerve, the probe having a microchannel which induces the regeneration of the nerve,
   wherein an electrode is installed within the microchannel and is physically isolated from gliosis, and the microchannel is configured to receive a nerve growth factor for regenerating the nerve, and
   when the probe is inserted into the nerve, the electrode physically isolated from gliosis accomplishes neural signal acquisition and stimulation.

2. The neural probe array according to claim 1, further comprising:
   a connecting body to which the probe is coupled, the connecting body having an elastic element formed in a meander shape.

3. The neural probe array according to claim 2, wherein the connecting body is configured to receive a wire electrically connected to the electrode, and
   the neural probe array further comprises a connector connected to the connecting body, the connector having a terminal electrically connected to the wire.

4. The neural probe array according to claim 1, wherein the microchannel is formed perpendicular to a lengthwise direction of the probe.

5. The neural probe array according to claim 1, wherein the nerve is a peripheral nerve.

6. The neural probe array according to claim 1, wherein the probe comprises:
   a support forming one surface of the probe;
   a first member provided on one surface of the support, and having an electrode receiving element in which the electrode is received;
   a second member connected to the first member, and having the microchannel; and
   a third member connected to the second member, and disposed opposite the first member with the microchannel interposed between.

7. The neural probe array according to claim 6, wherein the probe is a double layer structure having same shapes in combination.

8. The neural probe array according to claim 6, wherein each of the support and the first member has a cutout to communicate with the microchannel.

\* \* \* \* \*